(12) United States Patent
Choi et al.

(10) Patent No.: US 11,488,300 B2
(45) Date of Patent: Nov. 1, 2022

(54) IVUS IMAGE ANALYSIS METHOD

(71) Applicant: MEDI WHALE INC., Seoul (KR)

(72) Inventors: Tae Geun Choi, Seoul (KR); Geun Yeong Lee, Seoul (KR)

(73) Assignee: MEDI WHALE INC., Seoul (KR)

( * ) Notice: Subject to any disclaimer, the term of this patent is extended or adjusted under 35 U.S.C. 154(b) by 0 days.

(21) Appl. No.: 16/959,886

(22) PCT Filed: Dec. 7, 2018

(86) PCT No.: PCT/KR2018/015576
§ 371 (c)(1),
(2) Date: Jul. 2, 2020

(87) PCT Pub. No.: WO2019/135501
PCT Pub. Date: Jul. 11, 2019

(65) Prior Publication Data
US 2021/0090249 A1    Mar. 25, 2021

(30) Foreign Application Priority Data

Jan. 3, 2018  (KR) .................. 10-2018-0000799

(51) Int. Cl.
*G06T 7/00*        (2017.01)
*G06T 7/11*        (2017.01)
(Continued)

(52) U.S. Cl.
CPC .......... *G06T 7/0012* (2013.01); *A61B 8/0891* (2013.01); *A61B 8/12* (2013.01);
(Continued)

(58) Field of Classification Search
None
See application file for complete search history.

(56) References Cited

U.S. PATENT DOCUMENTS

2005/0249391 A1* 11/2005 Kimmel ............... G06T 7/11
                                                          382/128
2006/0036167 A1   2/2006 Shina
(Continued)

FOREIGN PATENT DOCUMENTS

| JP | 2007-512862 A | 5/2007 |
| KR | 10-2016-0079127 A | 7/2016 |
| KR | 10-2017-0021558 A | 2/2017 |

OTHER PUBLICATIONS

Arash Taki, Alireza Roodaki, Seyed Kamaledin Setarehdan, Sara Avansari, Gozde Unai, Nassir Navab, An IVUS image-based approach for improvement of coronary plaque characterization, Computers in Biology and Medicine, vol. 43, Issue 4, 2013, pp. 268-280 (Year: 2013).*

(Continued)

*Primary Examiner* — Vu Le
*Assistant Examiner* — Courtney Joan Nelson
(74) *Attorney, Agent, or Firm* — Fenwick & West LLP

(57) ABSTRACT

Disclosed in an intravascular ultrasound (IVUS) image analysis method, comprising the steps of: allowing a computer to acquire an IVUS image of an object; segmenting a constituent element included in the IVUS image; and determining the constituent parts and the degree of risk of plaque included in the IVUS image.

19 Claims, 9 Drawing Sheets

(51) Int. Cl.
*G06T 7/70* (2017.01)
*G16H 50/30* (2018.01)
*A61B 8/08* (2006.01)
*A61B 8/12* (2006.01)

(52) U.S. Cl.
CPC .................. *G06T 7/11* (2017.01); *G06T 7/70* (2017.01); *G16H 50/30* (2018.01); *G06T 2207/10132* (2013.01); *G06T 2207/20081* (2013.01); *G06T 2207/30101* (2013.01)

(56) References Cited

U.S. PATENT DOCUMENTS

| | | | |
|---|---|---|---|
| 2007/0165916 | A1 | 7/2007 | Cloutier et al. |
| 2014/0276684 | A1* | 9/2014 | Huennekens .. A61B 17/320758 606/7 |
| 2016/0367216 | A1* | 12/2016 | Yan ........................... G06T 7/30 |
| 2017/0049419 | A1* | 2/2017 | Park ....................... A61B 5/055 |

OTHER PUBLICATIONS

PCT International Search Report and Written Opinion, PCT Application No. PCT/KR2018/015576, dated Mar. 13, 2019, 11 pages (with English translation of International Search Report).
Korean Office Action, Korean Application No. 10-2018-0000799, dated Aug. 21, 2019, 12 pages.

\* cited by examiner

IVUS IMAGE ANALYSIS METHOD

TECHNICAL FIELD

The present invention relates to an intravascular ultrasound (IVUS) image analysis method.

BACKGROUND ART

Intravascular ultrasound (IVUS), also known as endovascular ultrasound, is used to insert a catheter having an ultrasound device into blood vessels and acquire ultrasound images of the interior of the blood vessels.

Acquired IVUS images are reviewed by doctors and are mainly used to quantitatively determine patients' coronary artery diseases or stenosis levels.

In the case of an experienced expert, some necessary information can be acquired using only IVUS images, but virtual histology (VH)-IVUS or near-infrared spectroscopy (NIRS) is also used to assist with the acquisition.

Recently, development has been actively conducted on a method of processing various medical images using deep learning to acquire necessary information.

Deep learning is defined as a set of machine-learning algorithms that attempt high-level abstraction (which is a task of abstracting key content or functions in a large amount of data or complex data) through a combination of several nonlinear transformation methods. In the big picture, deep learning can be seen as a field of machine learning that teaches human ways of thinking to computers.

DISCLOSURE

Technical Problem

The present invention is directed to providing an intravascular ultrasound (IVUS) image analysis method.

Technical problems to be solved by the present invention are not limited to the aforementioned problem, and other problems that are not mentioned here can be clearly understood by those skilled in the art from the following description.

Technical Solution

IVUS image analysis method according to an aspect of the present invention for solving the above mentioned problems, may comprise obtaining, by computer, an IVUS (IntraVascular UltraSound) image of a target, performing segmentation of components included in the IVUS image, determining constituents and a degree of risk of plaque included in the IVUS image.

Also, the step performing the segmentation may comprise performing the segmentation of the components included in the IVUS image using a model trained using labeled IVUS image.

Also, The IVUS image analysis method, may further comprise, determining location of the plaque included in the IVUS image.

Also, the IVUS image analysis method, may further comprise, presenting blood vessel in predetermined range of the target and presenting the determined location of the plaque in the presented blood vessel.

Also, the IVUS image analysis method, may further comprise, presenting a risk zone, based on the location of the plaque and the constituents and the degree of risk of the plaque.

Also, the step determining the constituents of the plaque may further comprise, determining the constituents of the plaque using a model trained using labeled IVUS image and processed IVUS image.

Also, the processed IVUS image may include, at least one of an image in which elements included in the IVUS image are marked differently according to the constituents or an image which is made by combining the NIRS (Near Infra-Red Spectroscopy) result to the IVUS image.

Also, the step determining the degree of risk of the plaque may further comprise, determining the degree of the risk of the plaque based on the constituents of the plaque.

Also, the step determining the degree of risk of the plaque may further comprise, determining the degree of the risk of the plaque using a model trained using IVUS image labeled with a presence or absence of a cardio-crerbrovascular disease.

According to an aspect of the present invention for solving the above-described problem, a computer program stored in a computer readable media to perform the method of claim 1 in combination with a computer that is hardware is provided.

Other specifics of the invention are included in the detailed description and drawings.

Advantageous Effects

According to the disclosed embodiment, it is possible to automatically determine the location, constituents, and degree of risk of plaques which are difficult to visually determine using the IVUS image.

Advantageous effects of the present invention are not limited to the aforementioned effects, and other advantageous effects that are not described herein will be clearly understood by those skilled in the art from the following description.

MODE FOR CARRYING OUT THE INVENTION

Figure 1:
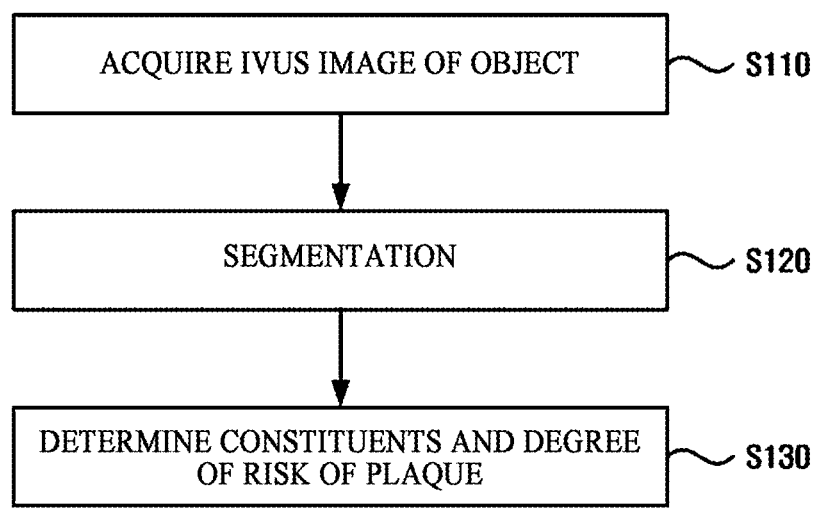
FIG. 1 is a flowchart showing an intravascular ultrasound (IVUS) image analysis method according to an embodiment.

Advantages and features of the present invention and implementation methods thereof will be clarified through the following embodiments described in detail with reference to the accompanying drawings. However, the present invention is not limited to embodiments disclosed herein and may be implemented in various different forms. The embodiments are provided for making the disclosure of the present invention thorough and for fully conveying the scope of the present invention to those skilled in the art. It is to be noted that the scope of the present invention is defined by the claims.

The terminology used herein is for the purpose of describing particular embodiments by way of example only and is not intended to be limiting to the disclosed invention. As used herein, the singular forms "a," "an," and "one" include the plural unless the context clearly indicates otherwise. The terms "comprises" and/or "comprising" used herein specify the presence of stated elements but do not preclude the presence or addition of one or more other elements. Like reference numerals refer to like elements throughout the specification, and the term "and/or" includes any and all combinations of one or more of the associated listed items. It will be also understood that, although the terms first, second, etc. may be used herein to describe various elements, these elements should not be limited by these terms. These terms are only used to distinguish one element from another. Thus, a first element could be termed a second element without departing from the technical spirit of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The term "unit" or "module" used herein refers to a software element or a hardware element such as a field-programmable gate array (FPGA) or an application-specific integrated circuit (ASIC), and a "unit" or "module" performs any role. However, a "unit" or "module" is not limited to software or hardware. A "unit" or "module" may be configured to be in an addressable storage medium or to execute one or more processors. Accordingly, as an example, a "unit" or "module" includes elements such as software elements, object-oriented software elements, class elements, and task elements, processes, functions, attributes, procedures, sub-routines, segments of program codes, drivers, firmware, micro-codes, circuits, data, database, data structures, tables, arrays, and variables. Furthermore, functions provided in elements and "units" or "modules" may be combined as a smaller number of elements and "units" or "modules" or further divided into additional elements and "units" or "modules."

Spatially relative terms, such as "below," "beneath," "lower," "above," "upper," "on," "between," and the like, may be used herein for ease of description to describe the relationship of one element to another element(s) as illustrated in the figures. It will be understood that the spatially relative terms are intended to encompass different orientations of elements in use or operation in addition to the orientation depicted in the figures. For example, if an element shown in the drawing is turned over, an element described as "below" or "beneath" another component could be placed "above" the element. Thus, the exemplary term "below" or "beneath" may encompass both orientations of "above" and "below" or "beneath." An element may be otherwise oriented and the spatially relative descriptors used herein interpreted accordingly.

The term "image" used herein may refer to multi-dimensional data composed of discrete image elements (e.g., pixels in a two-dimensional (2D) image and voxels in a three-dimensional (3D) image).

The term "object" used herein may refer to a person or animal or the entirety or a part of a person or an animal. For example, an object may include at least one of blood vessels and organs such as liver, heart, uterus, brain, breast, and abdomen. Also, an "object" may be a phantom. A phantom refers to a material having a volume very close to the effective atomic number and density of an organism and may include a sphere phantom having properties similar to a human body.

The term "user" used herein may refer to a doctor, a nurse, a clinical pathologist, or a medical imaging expert as a medical expert or may refer to a technician who repairs a medical device, but the present invention is not limited thereto.

Hereinafter, embodiments of the present invention will be described in detail with reference to the accompanying drawings.

FIG. 1 is a flowchart showing an intravascular ultrasound (IVUS) image analysis method according to an embodiment.

In the disclosed embodiment, each step shown in FIG. 1 is performed by a computer, and the term "computer" used herein encompasses a computing device including at least one processor.

In step S110, a computer acquires an IVUS image of an object.

Figure 2:
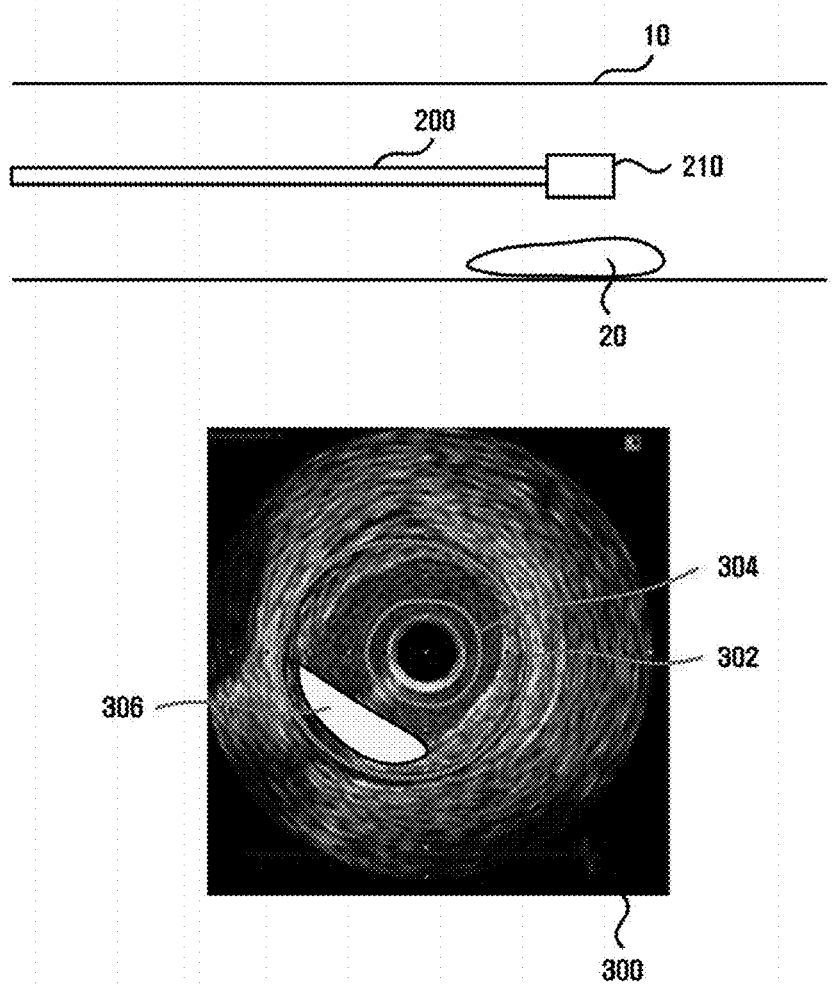
FIG. 2 is a diagram showing an example of a method of acquiring an IVUS image.

In the disclosed embodiment, the computer may be directly connected to an IVUS imaging apparatus in a laboratory or may acquire an IVUS image remotely through a network or server Referring to FIG. 2, an example of a method of acquiring an IVUS image is shown.

In detail, referring to FIG. 2, an example of acquiring an IVUS image 300 by inserting a catheter 200 into a blood vessel 10 is shown.

An ultrasonic transducer 210 rotating at high speed is provided at the end of the catheter 200 and is used to acquire an ultrasound image of the interior of the blood vessel 10. The acquired ultrasound image is used to derive opinions about the inner diameter, area, shape, blood vessel wall thickness, atheroma, plaque components, and blood clots of the blood vessel 10.

In an embodiment, a plaque 20 may be in the blood vessel 10.

The plaque 20 is cholesterol selectively absorbed and accumulated on the inner wall (lumen) of the blood vessel 10, and intravascular cell debris, smooth muscle cells, and macrophages are accumulated while a plaque is being formed. The accumulated plaque calcifies and protrudes into the blood vessel and thus may interfere with blood flow.

Referring to the IVUS image 300, the shape of the blood vessel and the accumulation of the plaque can be seen.

For example, an outer wall 302 (vessel), an inner wall 304, and a plaque 306 can be seen in the IVUS image 300. The IVUS image 300 may be analyzed and used by skilled medical personnel.

In an embodiment, the IVUS image 300 may be stored with the labeling of the locations of the inner and outer walls, and furthermore, the location of the plaque for the purpose of learning.

In step S120, the computer segments the elements included in the IVUS image 300 acquired in step S110.

In an embodiment, the computer segments the locations of the inner wall and the outer wall of the blood vessel included in the IVUS image 300.

Figure 3:
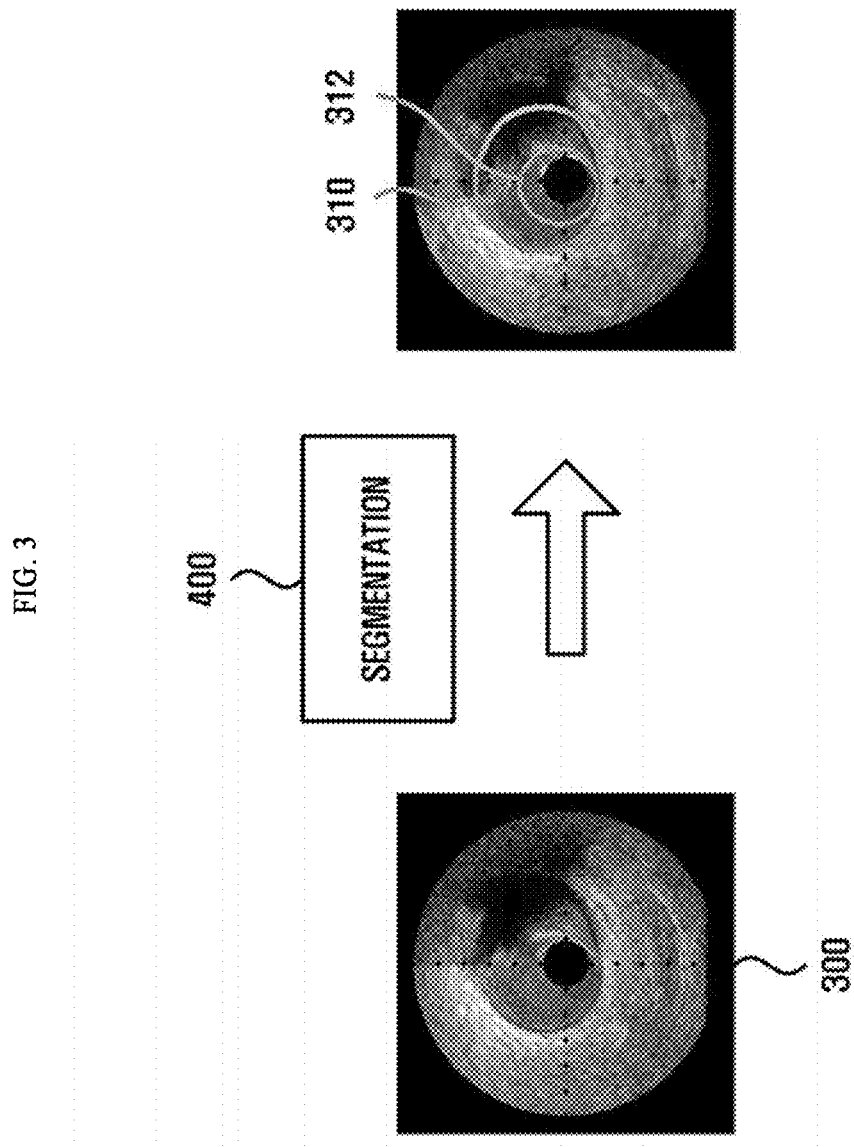
FIG. 3 is a diagram showing an example of a computer segmenting an IVUS image.

Referring to FIG. 3, an example of the computer segmenting the IVUS image 300 is shown.

In an embodiment, the computer segments the elements included in the IVUS image 300 using a model 400 which is trained using labeled IVUS images.

For example, the labeled IVUS images may be images in which the locations of the inner wall and the outer wall of the blood vessel are marked, and the trained model 400 may be a model that is trained by performing deep learning using the labeled IVUS images.

In an embodiment, the trained model 400 may be a model that uses U-NET.

U-NET is a kind of convolutional neural network that performs quick and accurate segmentation and is primarily used to segment medical images.

The model 400 outputs a result image obtained by segmenting the IVUS image 300. There is no limitation on the shape of the output image, and by using the resulting image, the computer may acquire an image obtained by adding the outer wall 310 and the inner wall 312 to the original IVUS image 300 as shown in FIG. 3.

In step S130, the computer determines the degree of risk and constituents of a plaque included in the IVUS image acquired in step S110.

As shown in FIG. 2, the outer wall 302 and the inner wall 304 of the blood vessel are represented in the IVUS image 300, and thus it is possible to visually check the degree of thickening of the blood vessel walls. Skilled experts can also estimate the location and composition of plaques contained in the thickened blood vessel even with the naked eye, but since this is not an accurate analysis, a means for assisting with determination is used.

Figure 4:
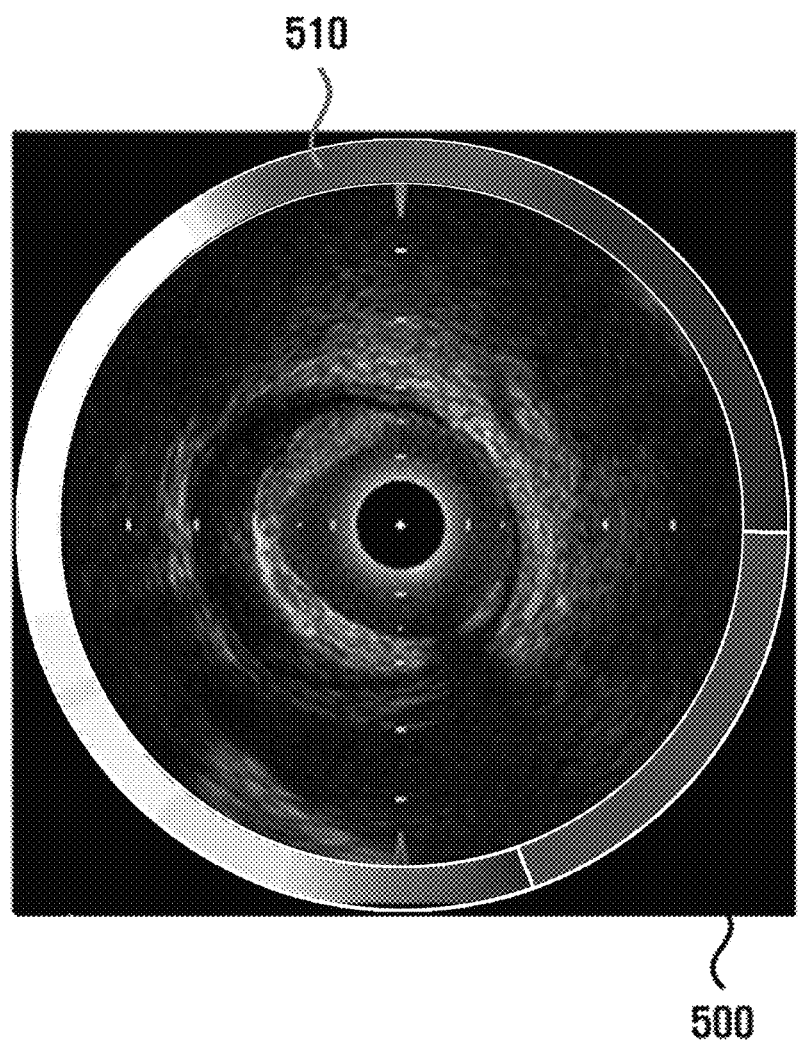
FIG. 4 is a diagram showing an example of a method of providing additional information for an IVUS image using near-infrared spectroscopy (NIRS).

Referring to FIG. 4, an example of a method of providing additional information for an IVUS image using near-infrared spectroscopy (NIRS) is shown.

NIRS is an examination method that can determine the composition of an object through a spectrum obtained by emitting near-infrared rays. In the disclosed embodiment, the method is used to examine a blood vessel wall to mark the location of a lipid component.

Among the plaques, lipid-containing plaques cause arteriosclerosis and other cardiovascular diseases, so it is important to know the locations and amount of the lipid-containing plaques to determine a patient's vascular health.

In an embodiment, as shown in FIG. 4, an NIRS image 510 which is a result obtained by using NIRS and in which a part containing lipid is represented in yellow may be provided together with an IVUS image 500, and thus it is possible for a user to accurately understand the composition of the plaque through the NIRS image 510.

As an example, the image shown in FIG. 4 may be acquired using TVC.

A TVC image is acquired by a TVC image system of Infraredx Inc. and provides information on the size and chemical composition of a lesion through near-infrared spectroscopy and ultrasound images of the interior of blood vessels.

Hereinafter, a TVC image is used as a term referring to an ultrasound image of the interior of a blood vessel and an image acquired through near-infrared spectroscopy and is not necessarily limited to an image obtained by a TVC image system of Infraredx Inc. In this specification, the term "IVUS-NIRS image" is also used in the same sense as the term "TVC image."

Figure 5:
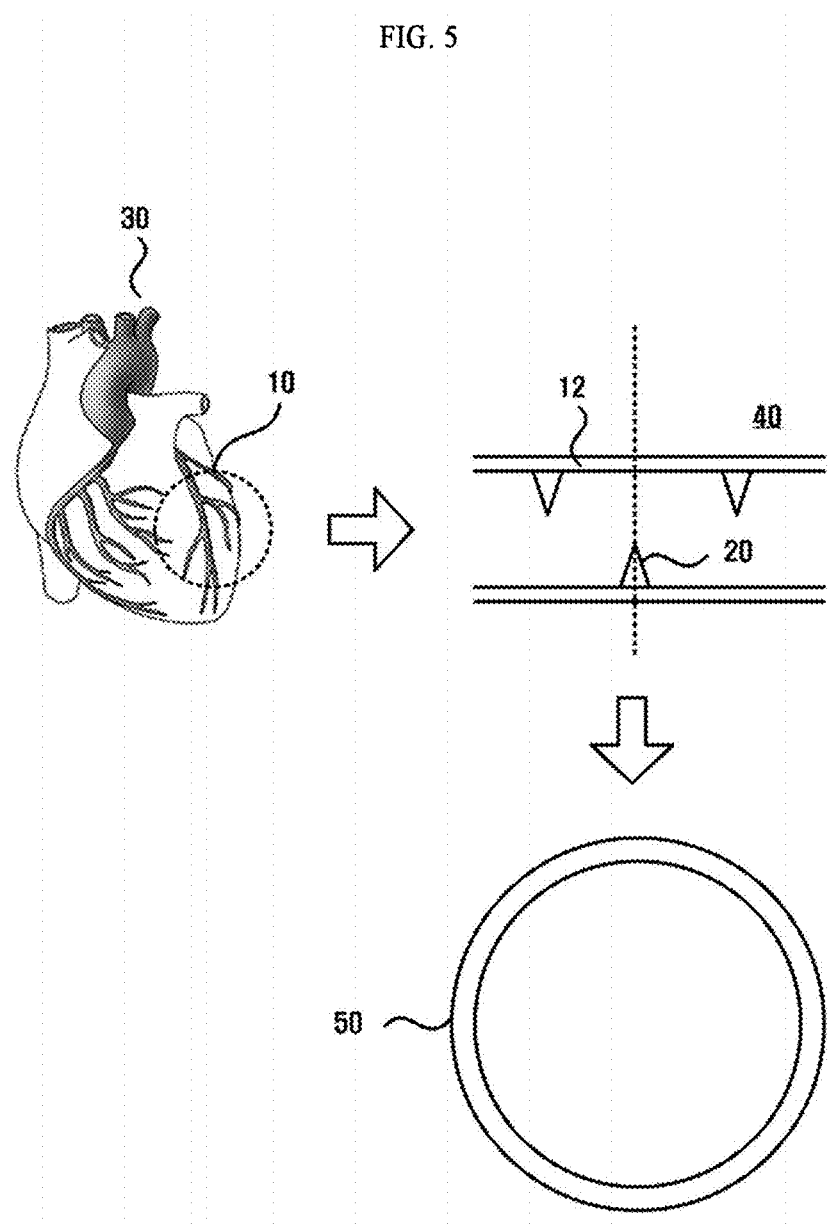
FIG. 5 is a diagram showing an example of acquiring a TVC image.

FIG. 5 is a diagram showing an example of acquiring a TVC image.

Referring to FIG. 5, the heart 30 of an object is shown.

A TVC image is acquired using near-infrared spectroscopy and ultrasound images of the interior of a coronary artery. By using a TVC image, it is possible to acquire sectional views of a coronary artery 10 from different viewpoints as shown in FIG. 5.

Referring to a cross-sectional view 40 shown in FIG. 5, the locations of a plaque 20 and a blood vessel wall 12 of the coronary artery 10 are shown. The locations of the blood vessel wall 12 and the plaque 20 may be displayed in specific shapes or as visualized images, as shown in FIG. 5, or may be colored as shown in FIG. 4. Accordingly, it is possible for the user to easily determine a location where a plaque is formed in the coronary artery 10 or where stenosis progresses.

Also, by using TVC, a longitudinal sectional view 50 having a different form may be acquired. Referring to the longitudinal sectional view, along with an IVUS image corresponding to one section in the coronary artery 10, information about the composition of the plaque is displayed on the edge of the IVUS image. The longitudinal sectional view 50 corresponds to the NIRS image 510 shown in FIG. 4.

In an embodiment, the computer may estimate and generate a TVC image including an NIRS analysis result from the IVUS image.

Figure 6:
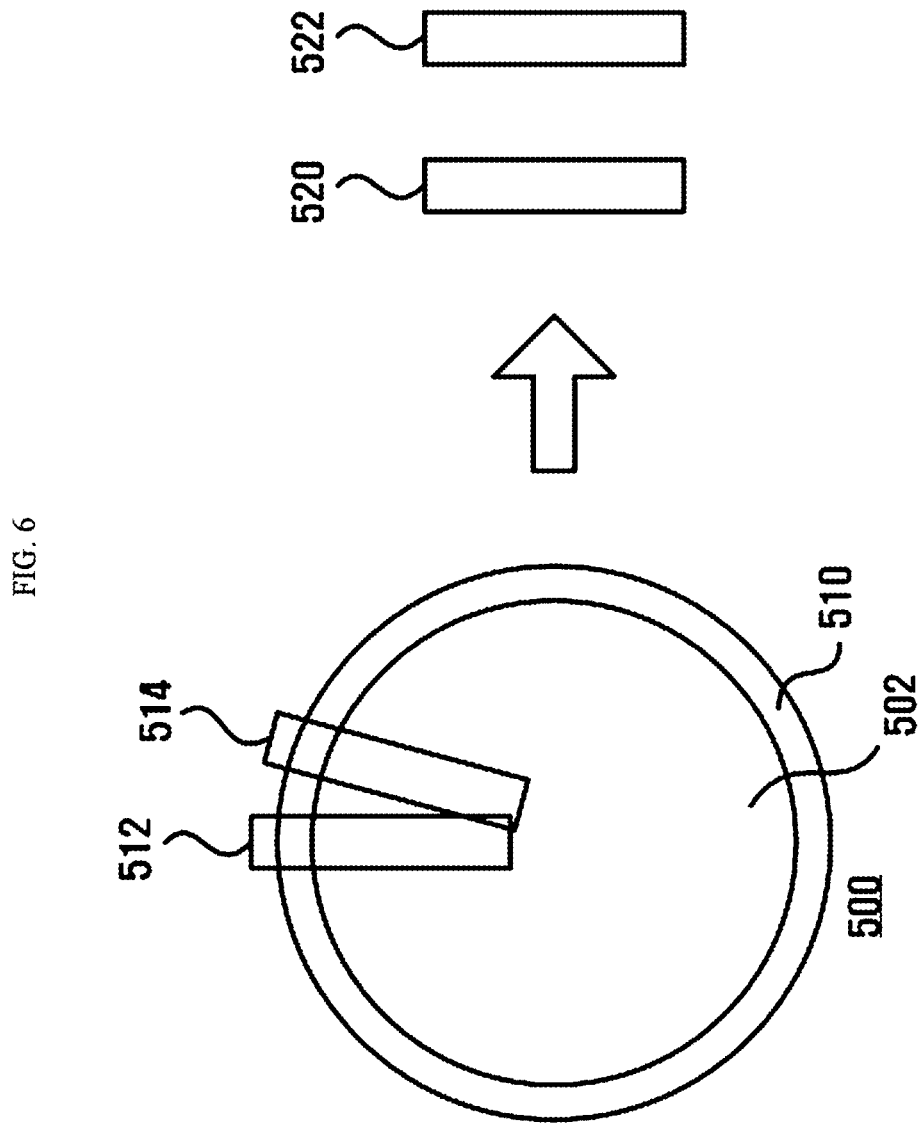
FIG. 6 is a diagram showing an example of a method of training a model for acquiring a TVC image from an IVUS image of a coronary artery.

FIG. 6 is a diagram showing an example of a method of training a model for acquiring a TVC image from an IVUS image of a coronary artery.

A TVC image 500 of a coronary artery of an object is shown in FIG. 6. The TVC image 500 may be divided into a part 502 indicating the interior of a blood vessel, which can be acquired using IVUS, and a part 510 indicating the characteristics of a plaque inside the blood vessel, which can be acquired using NIRS.

In an embodiment, the computer may cut the TVC image 500 at a predetermined angle. For example, as shown in FIG. 6, the computer may split the TVC image 500 into rectangles 512 and 514 which are inclined 10 degrees from one another.

The computer may determine the composition of a plaque contained in each rectangle using the part 510 indicating the characteristics of the plaque inside the blood vessel which is included in the corresponding rectangle.

For example, as shown in FIG. 6, the rectangles 512 and 514 may be processed into pieces of learning data 520 and 530 labeled on the basis of the composition of each plaque.

For example, the pieces of learning data 520 and 530 may be labeled on a color basis. For example, in the case of using NIRS, lipid-containing plaques are represented in yellow, and the other plaques are represented in red or brown. Accordingly, it is possible to label learning data based on color and perform learning.

In an embodiment, the computer may recognize the colors of the rectangles 512 and 514 to automatically generate labeled pieces of learning data 520 and 530.

The computer trains the model with the labeled pieces of learning data 520 and 530.

When a new IVUS image is acquired, the computer cuts the acquired IVUS image at a predetermined angle, inputs image cuts to the trained model, and acquires the composition of a plaque included in each image cut. There is no limitation to the output method of the trained model, and the composition of the plaque included in the image cut may be output using a numerical value, color, or the like.

The computer may estimate and acquire a TVC image from the IVUS image on the basis of a result of determining the image cuts.

In an embodiment, the computer determines the location of a plaque included in an IVUS image. The computer may determine the location of a plaque included in a single IVUS image. For example, the computer may segment a single IVUS image and then determine and display the location of a plaque.

Also, the computer may determine and display the location of a plaque in a blood vessel within a predetermined range of an object using consecutive IVUS images. For example, the computer may schematically display a blood vessel within a predetermined range 10 as shown in FIG. 5 but may determine and display the location of a plaque as shown in the cross-sectional view 40.

In the disclosed embodiment, virtual histology (VH)-IVUS may be used as a secondary means for the user or computer to determine the location and composition of the plaque.

Figure 7:
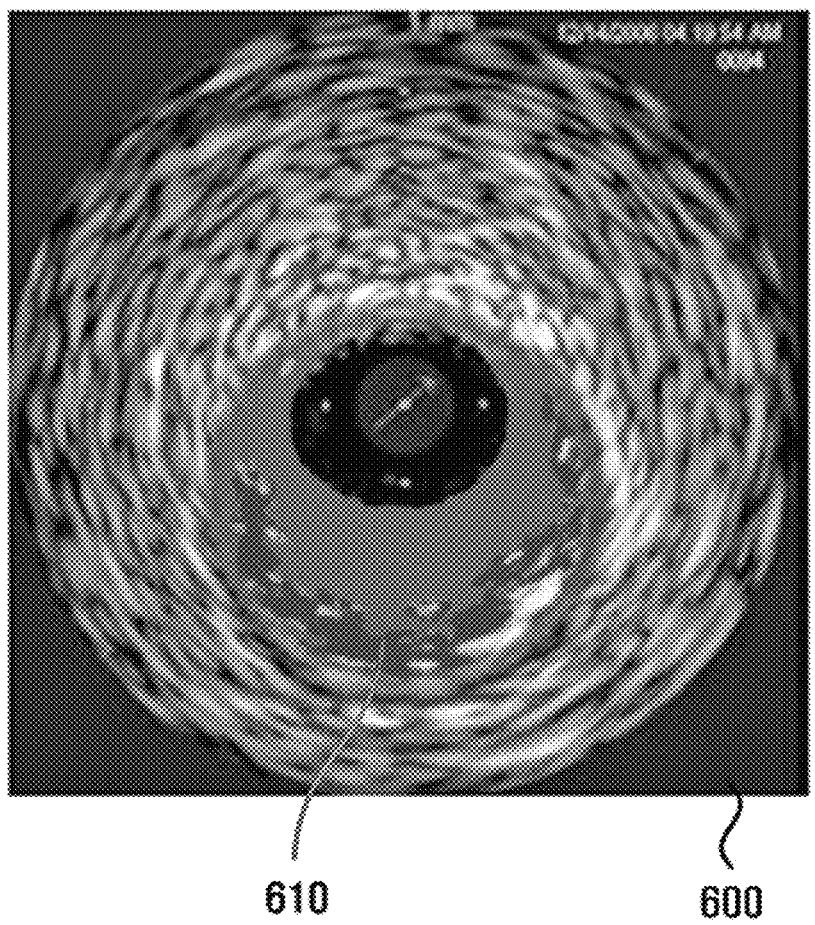
FIG. 7 is a diagram showing an example of a virtual histology (VH)-IVUS image.

Referring to FIG. 7, an example of a VH-IVUS image is shown.

In the disclosed embodiment, a VH-IVUS image collectively refers to an image in which each element included in an IVUS image is displayed differently depending on the composition and is not limited to an image acquired using a specific company or specific equipment.

For example, a VH-IVUS image may refer to a result obtained by coloring the composition of the plaque included in the IVUS image.

In the disclosed embodiment, a VH-IVUS image may be utilized as learning data for determining the location and composition of the plaque.

Figure 8:
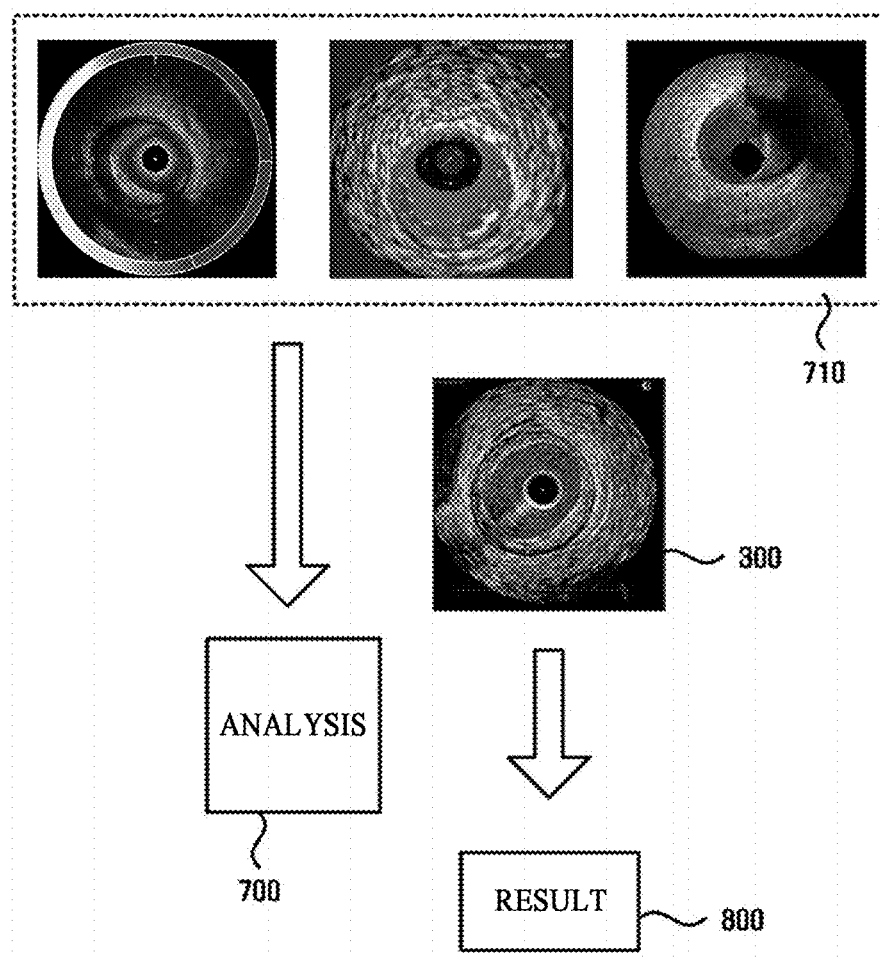
FIG. 8 is a diagram showing a method of analyzing an IVUS image according to an embodiment.

FIG. 8 is a diagram showing a method of analyzing an IVUS image according to an embodiment.

Referring to FIG. 8, an example of training a model 700 using learning data 710 is shown.

In an embodiment, at least one of an original IVUS image, a labeled IVUS image, a VH-IVUS image, and an IVUS-NIRS image may be used as the learning data 710. In addition, various data may be utilized as the learning data.

The model 700 may be trained through deep learning using the learning data 710, and there is no limitation on the specific training method.

In an embodiment, the IVUS-NIRS image is learned using the method described with reference to FIGS. 5 and 6, the VH-IVUS may be learned in the same way or a similar way to the labeled IVUS image, and the VH-IVUS image may be utilized as secondary data used to label the IVUS image.

The computer may analyze the IVUS image 300 using the trained model 700 and acquire the analysis result 800.

The analysis result 800 may be acquired in the form of an IVUS image in which the location and composition of the plaque are represented, for example, an image similar to a VH-IVUS image or an IVUS-NIRS image, and may also be acquired as separate analysis data. The analysis data may be acquired in the form of an image and may also be acquired in the form of text containing numbers.

In an embodiment, pre-processing and data cleaning of the learning data 710 may be performed first.

For example, a labeling task may be performed as the preprocessing of the learning data 710, and incorrect or inappropriate images may be excluded from the learning data.

In an embodiment, when unclassified learning data is acquired, the computer may classify whether each image included in the learning data is an IVUS image, a labeled IVUS image, a VH-IVUS image, or an IVUS NIRS image.

A classifier for classifying the learning data may be generated through training, and the computer may classify each image on the basis of the characteristics of the corresponding image. In this case, whether the learning data is correctly classified in the pre-processing process for the learning data may be determined.

In an embodiment, the feedback of the analysis result 800 may be performed. For example, feedback on whether the analysis result 800 is reviewed by the user and analyzed correctly or whether the analysis result is valid may be received.

In another embodiment, the feedback process may be automatically performed by analyzing the IVUS image included in the learning data 710 using the trained model 700 as part of the learning process and then by comparing the analysis result 800 to the learning data 710.

The computer may perform reinforcement learning on the model 700 on the basis of the above-described feedback result.

In an embodiment, the computer may determine the degree of risk of a plaque included in a blood vessel of an object on the basis of the IVUS image 300.

In an embodiment, the computer may determine the constituents of the plaque included in the blood vessel of the object using the above-described method and may determine the degree of risk of the plaque on the basis of the determined constituent.

For example, when the plaque contains lipid, the computer may determine that the plaque is in danger.

In an embodiment, the computer may label each IVUS image with information on a health status of an object of which the corresponding IVUS image is captured. For example, the computer may label an IVUS image with a health status of an object of which the IVUS image is captured, the health status including information about a cardiovascular disease of the object.

The computer may acquire the trained model using the IVUS image labeled with the health status of the object.

The computer may infer and acquire whether an object has a cardiovascular disease by inputting the IVUS image to the trained model. Likewise, by inputting the IVUS image to the trained model, the computer may determine whether a plaque included in the IVUS image causes the object's cardiovascular disease. That is, the computer may input the IVUS image to the trained model to determine the degree of risk of the plaque included in the IVUS image.

Figure 9:
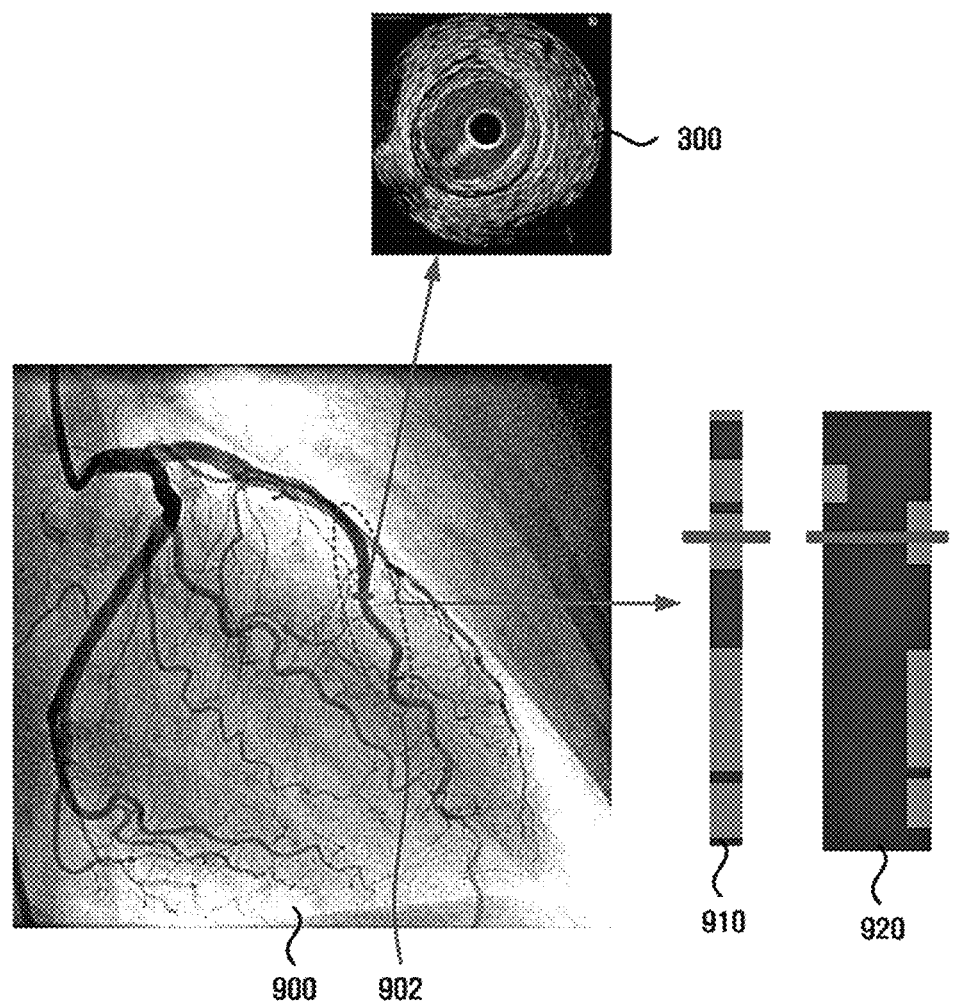
FIG. 9 is a diagram showing a result of analyzing an IVUS image according to an embodiment.

FIG. 9 is a diagram showing a result of analyzing an IVUS image according to an embodiment.

The computer may acquire one or more IVUS images 300 of at least a portion 902 of the object's cardiovascular artery 900 and determine the location, composition, and degree of risk of the plaque included in the object's cardiovascular artery 902 on the basis of the acquired IVUS images.

In an embodiment, the computer may schematically display the location and composition of the plaque included in the object's cardiovascular artery 902 on the basis of the determination result. For example, like an image 910 shown in FIG. 9, the cardiovascular artery 902 may be schematized with different colors depending on the section, and a section in danger, which includes a plaque in danger (e.g., a lipid-containing plaque), may be marked (e.g., in yellow).

Also, like another image 920 shown in FIG. 9, the location and size of the plaque with risk may be displayed while the cardiovascular artery 902 is schematized with colors. Likewise, the computer may also schematize an image in three dimensions or in the form of a top view of a three-dimensional (3D) image, and thus can display the accurate location and size of the plaque with risk.

Also, the computer may directly display the location, size, sections with risk, and the like of the plaque in a cardiovascular image 900 (e.g., a coronary angiography image) of the object instead of a schematized image.

In an embodiment, the analysis method according to the disclosed embodiment may be used in real-time not only for examination but also for treatments and surgeries.

For example, when a cardiovascular stent treatment or a plaque removal treatment is performed on an object, a catheter for acquiring an IVUS image may also be equipped with equipment for the stent or plaque removal treatment.

According to the disclosed embodiment, since a computer automatically determines the location, composition, and degree of danger of a plaque using only an IVUS image, it is possible to check a location requiring a stent treatment or a plaque removal treatment in real-time.

A user can determine the type of a treatment required at a location into which a catheter is inserted on the basis of information acquired in real-time and can immediately proceed with the treatment.

Therefore, by utilizing the disclosed embodiment, examination and treatment may be performed with only one invasive technique without needing to perform an invasive examination and an invasive treatment separately.

The steps of a method or algorithm described in connection with an embodiment of the present invention may be embodied directly in hardware, in a software module executed by hardware, or a combination of the two. A software mode may reside in random-access memory (RAM), read-only memory (ROM), erasable programmable ROM (EPROM), electrically erasable programmable ROM (EEPROM), flash memory, a hard disk, a removable disk, a CD-ROM, or any form of computer-readable recording medium that is known in the art.

Although embodiments of the present invention have been described with reference to the accompanying drawings, those skilled in the art will appreciate that various modifications and alterations may be made therein without departing from the technical spirit or essential feature of the present invention. Therefore, it should be understood that the above embodiments are illustrative rather than restrictive in all respects.

The invention claimed is:

1. A method of performing analysis of a cardiovascular image of a subject, comprising:
    obtaining a first image of at least a partial region of a cardiovascular of the subject; and
    obtaining a second image by processing the first image based on a diagnosis assistance model, the diagnosis assistance model being trained based on a first blood vessel image and a second blood vessel image corresponding to the first blood vessel image as a labeled data;
    wherein the first image and the first blood vessel image are taken with a same imaging method,
    wherein the second image is generated based on the first image to include analysis information on at least a partial region of the first image,
    wherein an object of the second blood vessel image corresponds to an object of the first blood vessel image,
    wherein a location of the cardiovascular vessel captured in the second blood vessel image corresponds to a location of the cardiovascular vessel captured in the first blood vessel image, and
    wherein the first blood vessel image and the second blood vessel image are taken with different imaging methods.

2. The method of claim 1, wherein the analysis information includes numerical information or color information based on a type of component of a plaque included in at least a partial region of the first image.

3. The method of claim 1, wherein the analysis information includes color information displayed so that a location of a lipid component and a blood vessel outer wall region included in the first image correspond when the analysis information includes information on whether a plaque contains a lipid component and a location of the lipid component.

4. The method of claim 1, wherein the analysis information is displayed in a first color indicating that a component of a plaque contains a lipid component or a second color indicating that the component of the plaque does not contain the lipid component, and wherein the first color and the second color are different.

5. The method of claim 1, wherein the diagnosis assistance model labels whether a plaque included in the second blood vessel image contains a lipid component, wherein the diagnosis assistance model is labeled with a third color when the plaque included in the second blood vessel image contains a lipid component, and wherein the diagnosis assistance model is labeled with a fourth color when the plaque included in the second blood vessel image does not contain a lipid component, and the third color and the fourth color are different.

6. The method of claim 1, wherein the diagnosis assistance model labels whether a plaque included in the second blood vessel image contains a lipid component and a location of the plaque.

7. The method of claim 1,
    wherein the first blood vessel image is divided into a plurality of first rectangular regions rotated at a predetermined angle of 10 degrees or less,
    wherein the second blood vessel image is divided into a plurality of second rectangular regions rotated at the predetermined angle,
    wherein the plurality of first rectangular regions and the plurality of second rectangular regions correspond to each other, respectively,
    wherein the diagnosis assistance model labels whether a plaque included in the second rectangular regions corresponding to the first rectangular regions contains a lipid component,
    wherein the diagnosis assistance model labels a location of the lipid component based on locations of the first rectangular regions and the second rectangular regions,
    wherein the diagnosis assistance model is labeled with a fifth color when the plaque included in the second rectangular regions contains a lipid component,
    wherein the diagnosis assistance model is labeled with a sixth color when the plaque included in the second rectangular regions does not contain a lipid component, and
    wherein the fifth color and the sixth color are different.

8. The method of claim 1,
    wherein the first blood vessel image is an ultrasound image of a cardiovascular, and
    wherein the second blood vessel image includes a result of near-infrared spectral spectrum of cardiovascular, a result of virtual histological analysis, or the first blood vessel image on which information of the object is labeled.

9. The method of claim 1,
wherein the diagnosis assistance model includes a classification model for classifying the second blood vessel image according to an image capturing device or labeling of the second blood vessel image, and
wherein information labeled on the first blood vessel image corresponding to the second blood vessel image is different according to a classification result of the classification model.

10. A non-transitory computer-readable storage medium storing instructions, the instructions when executed by a processor cause the processor to:
obtain a first image of at least a partial region of a cardiovascular of a subject; and
obtain a second image by processing the first image based on a diagnosis assistance model, the diagnosis assistance model being trained based on a first blood vessel image and a second blood vessel image corresponding to the first blood vessel image as a labeled data;
wherein the first image and the first blood vessel image are taken with a same imaging method,
wherein the second image is generated based on the first image to include analysis information on at least a partial region of the first image,
wherein an object of the second blood vessel image corresponds to an object of the first blood vessel image,
wherein a location of the cardiovascular vessel captured in the second blood vessel image corresponds to a location of the cardiovascular vessel captured in the first blood vessel image, and
wherein the first blood vessel image and the second blood vessel image are taken with different imaging methods.

11. An electronic device for analyzing a cardiovascular image of a subject comprising at least one processor configured to:
obtain a first image of at least a partial region of a cardiovascular of the subject, and
obtain a second image by processing the first image based on a diagnosis assistance model, the diagnosis assistance model being trained based on a first blood vessel image and a second blood vessel image corresponding to the first blood vessel image as a labeled data,
wherein the first image and the first blood vessel image are taken with a same imaging method,
wherein the second image is generated based on the first image to include analysis information on at least a partial region of the first image,
wherein an object of the second blood vessel image corresponds to an object of the first blood vessel image,
wherein a location of the cardiovascular vessel captured in the second blood vessel image corresponds to a location of the cardiovascular vessel captured in the first blood vessel image, and
wherein the first blood vessel image and the second blood vessel image are taken with different imaging methods.

12. The electronic device of claim 11, wherein the analysis information includes numerical information or color information based on a type of component of a plaque included in at least a partial region of the first image.

13. The electronic device of claim 11,
wherein the analysis information includes color information displayed so that the location of a lipid component and the blood vessel outer wall region included in the first image correspond, in case that the analysis information includes information on whether a plaque contains a lipid component and the location of the lipid component.

14. The electronic device of claim 11,
wherein the analysis information is displayed in a first color indicating that a component of a plaque contains a lipid component or a second color indicating that the component of the plaque does not contain a lipid component, and
wherein the first color and the second color are different.

15. The electronic device of claim 11,
wherein the diagnosis assistance model labels whether a plaque included in the second blood vessel image contains a lipid component,
wherein the diagnosis assistance model is labeled with a third color in case that the plaque included in the second blood vessel image contains a lipid component, and
wherein the diagnosis assistance model is labeled with a fourth color in case that the plaque included in the second blood vessel image does not contain the lipid component, and the third color and the fourth color are different.

16. The electronic device of claim 11, wherein the diagnosis assistance model labels whether a plaque included in the second blood vessel image contains a lipid component and a location of the plaque.

17. The electronic device of claim 11,
wherein the first blood vessel image is divided into a plurality of first rectangular regions rotated at a predetermined angle of 10 degrees or less,
wherein the second blood vessel image is divided into a plurality of second rectangular regions rotated at the predetermined angle,
wherein the plurality of first rectangular regions and the plurality of second rectangular regions correspond to each other, respectively,
wherein the diagnosis assistance model labels whether a plaque included in the second rectangular regions corresponding to the first rectangular regions contains a lipid component,
wherein the diagnosis assistance model labels a location of the lipid component based on locations of the first rectangular regions and the second rectangular regions,
wherein the diagnosis assistance model is labeled with a fifth color when the plaque included in the second rectangular regions contains a lipid component,
wherein the diagnosis assistance model is labeled with a sixth color when the plaque included in the second rectangular regions does not contain a lipid component, and
wherein the fifth color and the sixth color are different.

18. The electronic device of claim 11,
wherein the first blood vessel image is an ultrasound image of a cardiovascular, and
wherein the second blood vessel image includes a result of near-infrared spectral spectrum of cardiovascular, a result of virtual histological analysis, and the first blood vessel image on which information of an object is labeled.

19. The electronic device of claim 11,
wherein the diagnosis assistance model includes a classification model for classifying the second blood vessel image according to an image capturing device or labeling of the second blood vessel image, and
wherein information labeled on the first blood vessel image corresponding to the second blood vessel image is different according to a classification result of the classification model.

* * * * *